United States Patent [19]
Merlette

[11] Patent Number: 5,156,631
[45] Date of Patent: Oct. 20, 1992

[54] FOOT AND LEG PROSTHESIS AND METHOD OF MAKING SAME

[76] Inventor: John Merlette, 1208 E. Mockingbird La., Sandy, Utah 84070

[21] Appl. No.: 760,151

[22] Filed: Sep. 16, 1991

[51] Int. Cl.⁵ .......................... A61F 2/66; A61F 2/60
[52] U.S. Cl. ........................ 623/52; 623/55; 623/27
[58] Field of Search .............. 623/38, 47–56, 623/27

[56] References Cited

U.S. PATENT DOCUMENTS

| | | | |
|---|---|---|---|
| 366,494 | 7/1887 | Marks | 623/27 X |
| 4,268,922 | 5/1981 | Marsh et al. | 623/27 X |
| 4,547,913 | 10/1985 | Phillips | 623/27 |
| 4,822,363 | 4/1989 | Phillips | 623/27 |
| 4,959,073 | 9/1990 | Merlette | 623/55 |
| 5,037,444 | 8/1991 | Phillips | 623/55 |

FOREIGN PATENT DOCUMENTS

| | | | |
|---|---|---|---|
| 0156278 | 11/1903 | Fed. Rep. of Germany | 623/27 |
| 0494538 | 3/1930 | Fed. Rep. of Germany | 623/27 |
| 0690957 | 9/1930 | France | 623/27 |
| 0806023 | 2/1981 | U.S.S.R. | 623/55 |
| 2084025 | 4/1982 | United Kingdom | 623/47 |

Primary Examiner—Randall L. Green
Assistant Examiner—D. Willse
Attorney, Agent, or Firm—Mallinckrodt & Mallinckrodt

[57] ABSTRACT

A foot prosthesis and multi-step process for making same, has an upper main member and a sole member as dual segments of the prosthesis and arrangements for removably securing the prosthesis to a stump socket. The upper member has a U-shaped shank strut and flat ankle transition zone and an anterior toe section. The sole member has a plantar toe section and heel section. The invention is specially design to accommodate construction from fiberglass composite materials although the design will accommodate construction from other composite materials or even other materials that are not of the composite type.

The process for making the foot prosthesis comprises the steps of forming the two segments. Then the formed segments are bonded together using a compatible resilient elastomer material, such as a high elongation, polyurethane elastomer, a silicone adhesive, or fiber reinforced versions of such elastomers.

13 Claims, 3 Drawing Sheets

FOOT AND LEG PROSTHESIS AND METHOD OF MAKING SAME

BACKGROUND OF THE INVENTION

1. Field

The invention is in the field of foot prostheses which attach to an amputation socket and provide an artificial leg and foot for a wearer.

2. State of the Art

There are a number of different foot and leg prosthetic devices currently in use. The primary goal of these devices is to extend an amputated leg stump to the ground so as to support the wearer while upright and enable him to walk. The earliest prior art was merely a peg secured to the amputated limb which provided minimal mobility to the wearer. Later, a foot was added to the bottom of the peg.

Most prior art feet were constructed as either a single foot piece attached to a shank strut or a heel segment attached to a continuous shank and forefoot segment. An example of a more modern basic foot prosthesis is known as the "SACH" Foot, "SACH" standing for Solid Ankle Cushioned Heel. The "SACH" foot is a carved wooden foot with an aluminum leg strut for attaching the foot to the amputation socket. Additional improvements made to the basic device by way of ankle hinges or ball joints improved mobility. However, due to the rigidity and weight of the components, including the mechanical joints, such prostheses remained unnaturally heavy and stiff.

Recent improvements to foot prosthesis configurations utilize modern composite material technology to impart energy storage and release during use. Examples of these are the so called "Seattle Foot", which is a molded plastic foot, and the prosthesis shown in U.S. Pat. No. 4,547,913, known as the Flex-Foot, which provides a composite strut and foot configuration. The spring-like action imparted by the materials used results in additional mobility and comfort to the wearer. However, such prior art retains certain design characteristics which prohibit the use of inexpensive and lightweight fiberglass composite materials.

All known devices within this group are made up of individual components that must be fastened together, be it a separate sole or heel member to a foot member or a separate foot member to a connection leg extension strut member. These joints must be rigidly constructed so as to be strong enough to withstand the concentrated loads transmitted through them. The result is that local stiffness occurs, which interferes with smooth and even flexing of the components during the wearer's stride. Even with rigidly constructed joints, these devices are prone to fatigue and fracture at the joints, thus placing the wearer at risk of injury.

In addition, composite materials exhibit poor bearing strength where fasteners penetrate the construction. The accumulated wear and erosion of structural material surrounding fasteners result in loss of position or support of attached components after a period of continual use. The fastening of the heel to the ankle portion of the foot as in U.S. Pat. No. 4,547,913, occurs at the highly stressed ankle zone. To prevent fracture, the buildup of materials required for strength makes attractive cosmetic finishing of the ankle area difficult. Providing a structurally adequate, yet lightweight, cosmetically pleasing, and inexpensive ankle has long remained a problem.

Furthermore, while substantially lighter in weight and more natural in flexibility, the components of this type of prosthesis are generally significantly costlier than the prior art "SACH" type devices. It has long been desired to be able to use low priced, lightweight materials, such as fiberglass composite materials. However, the available inexpensive fiberglass composite materials lack the needed strength required for use in the prior art designs. By the term "fiberglass composite materials", it is to be understood that materials such as commercial grade, E-glass®, unidirectional and/or cross-plied fabrics embedded in resins, such as wet laminating epoxy resins and orthothalic and/or isothalic polyester resin matrix material, are intended.

SUMMARY OF THE INVENTION

A principle object in the making of the invention was to provide a design that can be constructed of lightweight, low priced fiberglass composite materials although the novel design of the invention could be constructed of other composite material such as carbon fiber or even other materials that are not of the composite type.

The design is particularly useful for overcoming the limitations in the strength of fiberglass and these limitations ar overcome by a variety of techniques. The fiberglass is layered to form a core of unidirectional fabric encapsulated in cross-plied fabric to use to best advantage the relative strengths of unidirectional and cross-plied fiberglass fabrics. For the shank strut section, where greater strength and resistance to bending rather than to torsion is required, a U-shaped construction is employed as well as a larger number of laminations. In the ankle and anterior forefoot sections more flexibility is desired, so fewer laminations in a flat shape are used.

The transition to a flat lamination in the ankle transition zone and on to fewer laminations approaching the toe tip results in great flexibility. Thus, smoother roll-over while ambulating and the desired "energy return" character is achieved.

The prosthesis of the invention is a dual segment prosthesis but unlike the dual segment prostheses of the prior art. The upper segment, referred to as the main member, has a leg or shank strut portion, an ankle transition zone, and an anterior toe section including an anterior upper toe section and an anterior toe tip. The other segment, the plantar foot or sole segment, comprises a plantar toe tip, plantar upper toe section, heel section, and heel tip. Constructing the two segments in this manner creates a greater surface area for bonding the two segments together. The two segments are joined together along adjacent upper toe and toe tip sections. When the two segments are constructed from fiberglass composite materials, the two segments are joined using a selected resilient material compatible with fiberglass such as a high elongation, polyurethane elastomer.

Bonding the two segments together with a high elongation polyurethane elastomer has advantages over the prior art. As one advantage, its elasticity allows the heel section of the sole segment to simulate natural flexion during ambulation on uneven terrain. For another advantage, the bonded joint avoids deterioration of the composite lamina of the associated drilled holes and mechanical fasteners of the prior art. As an associated advantage, the composite material is not built up to withstand the stress of mechanical joiners, thus enabling more satisfactory cosmesis. For still another advantage, the shock absorbency of the resilient material dissipates the shock load associated with heel strike Novel adapter arrangements for securing the shank of the prosthesis to a stump socket for receiving the residual, amputation stump were required because of the novel U-shaped shank strut. One novel arrangement includes an upright adapter fitting of tubular cross-section adapted to be received by the U-shaped shank strut. The upright adapter fitting can be received by a standard clamp type socket attachment which is commercially available. A novel means for securing the adapter fitting to a socket includes a mounting plate adapted for securing the adapter fitting to its lower surface and for securing a socket at least indirectly against its upper surface. There is preferably provided a spacer which horizontally spans the space between opposite surfaces of the adapter fitting and which is adapted to receive attachment mean for securing the adapter fitting to the shank strut of a prosthesis.

Another novel adapter arrangement includes an alternative adapter fitting coupling adapted to receive the shank strut of a prosthesis. This coupling may be adapted to receive a shank strut with U-shaped cross-section, circular cross-section, or some other cross-sectional shape. The upper surface of this coupling is adapted for attaching directly or indirectly to a socket. With this adapter fitting arrangement, there is preferably provided a spacer which bridges the space between opposite inside surfaces of a U-shaped shank strut or hollow tubular shank strut.

The former adapter arrangement including the mounting plate and the latter adapter arrangement are removably attached to a standard stump socket and extension. The extension includes a filler block, the upper portion of which is formed to receive said socket and is secured to same, the lower portion of which is formed to have receiving means within its matrix for receiving attachment means for removably securing either of said adapter arrangements.

THE DRAWINGS

The best mode presently contemplated for carrying out the invention commercially is illustrated in the accompanying drawing, in which:

FIG. 1 is a side view in vertical section taken through a fully assembled foot and leg prosthesis of the invention, the cosmetic covering of the prosthesis being indicated by broken lines;

FIG. 2, a similar view looking from the front of the prosthesis as shown in FIG. 1;

FIG. 3, a fragmentary view in horizontal section taken along the line 3—3 of FIG. 2 and drawn to a larger scale;

FIG. 4, a horizontal section taken on the line 4—4 of FIG. 2 and drawn to a larger scale than FIG. 2;

FIG. 5, a perspective view of an alternate shank strut attachment fitting coupling looking toward the top, front, and left side relative to FIG. 2 and drawn to the scale of FIG. 4;

FIG. 6, a top plan view of the coupling of FIG. 5, with a U-shaped shank strut inserted thereinto;

FIG. 7, a view in vertical section taken along the line 7—7 of FIG. 6; and

FIG. 8, a perspective view of the coupling of FIG. 5 looking toward the bottom and front wall thereof.

DETAILED DESCRIPTION OF THE ILLUSTRATED EMBODIMENT

Figure 1:
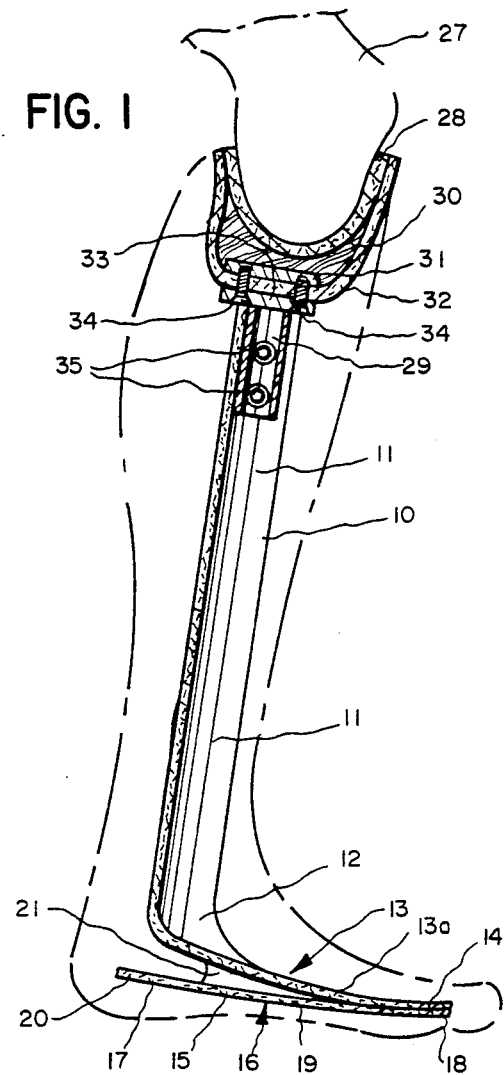
Figure 2:
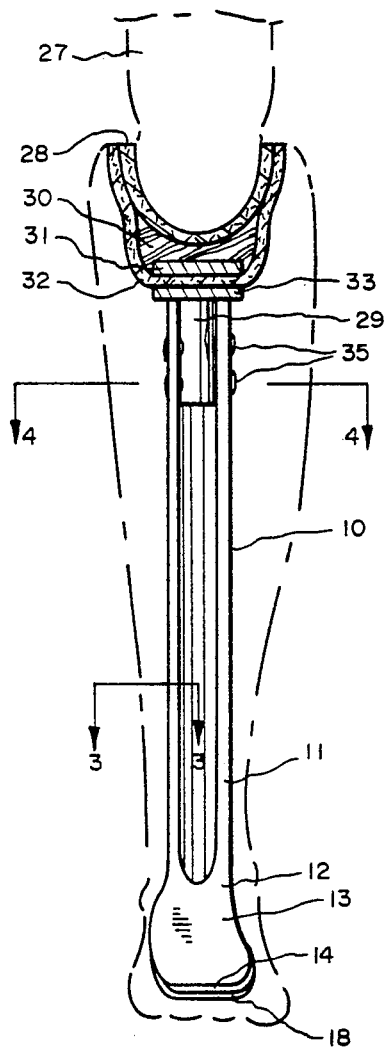
Figure 4:
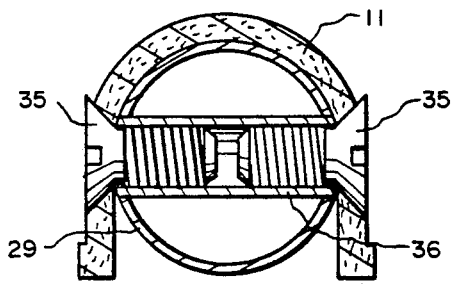

In the form illustrated, the foot and leg prosthesis of the invention comprises an elongate, composite, main member 10, FIGS. 1 and 2, having a shank strut section 11, ankle transition zone 12, and anterior toe section 13 including anterior upper toe section 13a extending to anterior toe tip 14. As shown in FIG. 4, shank strut section 11 has a U-shaped cross-sectional area. The size of the shank could vary a great deal but since other commercial devices having a tubular cross-section usually employ a shank of 30 mm outside diameter, the inside diameter of the U is preferably adapted to receive a tube of 30 mm outside diameter.

Likewise, the length of the shank strut can vary. As illustrated, the shank strut is of sufficient height to extend a below-the-knee amputation stump to the ground. Some amputations are farther below the knee than shown in FIGS. 1 and 2, and in those instances the shank strut section can simply be sawed off to the appropriate height. The shank strut may be made of greater height for above-the-knee amputees.

As shown in FIG. 1, sole member 15 is provided as a separate member having plantar toe section 16 and heel section 17. Plantar toe section 16 includes plantar toe tip 18 and plantar upper toe section 19 which extend approximately adjacent to anterior toe tip 14 and anterior upper toe section 13a then backwardly to heel section 17 and heel tip 20. As stated, plantar toe section 16 extends generally adjacent to anterior toe section 13. As anterior upper toe section 13a turns upwardly towards ankle transition zone 12, sole member 15 diverges to remain roughly parallel to the ground surface. Main member 10 and sole member 15 are designed to accomodate construction separately of fiberglass, continuous and woven, and/or short length fiber mat in a polyester or epoxy resin which surrounds and encapsulates the individual fibers. However, the design will accommodate other construction materials. Preferably, construction is with inexpensive fiberglass composite materials including E-glass ® unidirectional and cross-plied fabrics embedded in a resin matrix selected from the group of resins comprising orthothalic and isothalic polyester resin.

If fiberglass composite materials are employed, resilient material 21 must be compatible with said fiberglass composite material and is, preferably, a castable polyurethane resin. It is adhered between the adjacent portions of anterior toe section 13 of main member 10 and plantar toe section 16 of sole member 15. The choice of resilient material is crucial. Resilient material of the prior art, usually flexible rubber or neoprene, is incompatible with fiberglass/polyester but is compatible with the more expensive carbon fiber/epoxy composite materials of the prior art. Thus, such incompatible resilient material is replaced here in the preferred fiberglass embodiment by a polyurethane, a silicone adhesive, or similar such compatible materials with or without reinforcing fibers added. As shown in FIG. 1, resilient material 21 extends from the toe tips back to the area where anterior toe section 13 of main member 10 and plantar toe section 16 of sole member 15 diverge.

The preferred resilient material 21 is selected from among a family of elastomers including especially Adiprene ® L-42, L-100, and L-167 formulated by using Bisamine ® curing agent. Resilient material 21 may also be selected from other polyurethane resins and may have added to it milled glass fiber to harden and increase its tear strength. The various elastomers have varying degrees of resiliency, stiffness, strength, elongation properties, and durability and can be selected to suit specialized requirements. When the selected polyurethane is applied and cured, it provides an excellent bond to the cured composite surfaces.

Mechanical peel tests on the proposed material system were made. For the tests, Adiprene ® L-100 was used. Test coupons representative of joint 21 required between 756 and 922 pounds force to separate the bond. The preferred elastomer also exhibits high elongation properties, up to 800%, which allow substantial deflection of the composite components while maintaining joint integrity. Whichever compatible resilient material is selected, it must restrain and control relative movement between sole member 15 including heel tip 20 and the adjacent anterior upper toe and anterior toe tip sections.

Figure 3:
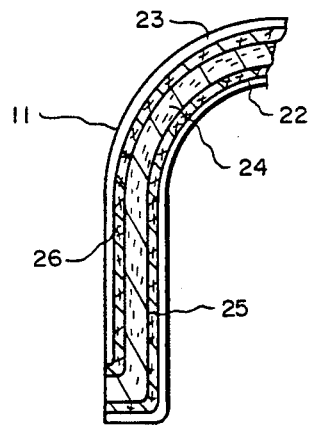

In construction of the prosthesis, conventional fiberglass materials and construction techniques are preferably employed. FIG. 3, an enlarged cross-section of shank strut section 11, shows a typical preferred foot construction. First, colorized "gelcoat" 22 and 23 is spray applied to the primary mold and to a lighter caul or secondary mold, respectively. On the finished foot, this gelcoat provides a smooth, attractive finish on anterior surface 22 and posterior surface 23 of the part, see FIG. 3. Although concealed during final cosmesis application, the protection from splinters and the aesthetics afforded by the gelcoat are desirable features. The same effect can, alternatively, be achieved using colorized fabrics or films. Alternatively, of course, the construction can be completed with no surface treatment at all.

The laminations of main member 10 and sole member 15 preferably comprise unidirectional fiberglass composite 24, which extends lengthwise, encapsulated by cross-plied composite made up of standard woven fabric layers 25 and 26, as shown in FIG. 3. The U-shape of the shank, combined with the unidirectional fibers within, provide bending stiffness and thus a sense of stability to the amputee. The cross-plied woven fabric at the surface provides torsional stiffness, i.e., resistance to movement, and resilience to return when deformation caused by applied load does occur.

The optimum number of plies in the laminate is attained when a small amount of bending or torsional deflection occurs under an applied load, with sufficient resistance and spring back when the load is released to simulate the behavior of the musculoskeletal system in the natural limb. The number of plies, i.e., layers, varies in the different sections from about eight in shank strut section 11, to about fifteen layers in ankle section 12, and to about three or four layers in the toe and heel tips.

Depending on the foot size and strength needed in a particular prosthesis, the number of plies employed can be increased or decreased as required. For example, fewer laminations may be required for a smaller prosthesis or a prosthesis for a light weight individual. A larger prosthesis or a prosthesis for a heavier individual may require more laminations. It is generally desirable to employ as few laminations as are needed for strength and stiffness to keep the prosthesis as light weight as practicable.

In the replication of the natural limb, greater bending deflection is desired in ankle transition zone 12 and anterior toe tip 14 than in shank strut section 11. The U-shape of shank strut section 11 causes greater resistance in bending than in torsion for a given laminate construction. It was necessary to modify the shank for greater resistance because of the lesser inherent rigidity of fiberglass compared to the prior art carbon fiber composite materials.

The transition to a flat lamination at ankle transition zone 12 allows for increased deflection under a given load in the forefoot as is desired. The reduction in the combined number of laminations and, thus, in the total laminate thickness, from ankle transition zone 12 to anterior toe tip 14 results in a further increase in flexibility. This flexibility results in a smoother rollover while ambulating. In other words, it is desirable for the toe to bend. If the toe were too stiff, the foot would elevate about a toe pivot instead of bending. Thus, it would cause an unnatural elevation of the leg and hip on the amputated side. Conversely, if the toe did not exhibit spring-like or "energy return" characteristics, the body would have to contort and expend excess energy to drag the prosthesis forward to achieve step-by-step mobility.

The attachment of prosthesis 10 to limb amputation 27 employs a novel adapter arrangement. By convention, socket 28 is provided as shown in FIG. 1. Socket 28 is a close fitting molding of heat formed plastic or rigid laminated composite. It is often padded to prevent chaffing to the residual, natural limb. It is first fitted to the patient. Often a commercial temporary alignment tool (not shown) is fitted to the socket. After angular and linear alignment is completed, the commercial alignment tool is usually transferred out and the novel adapter arrangement secures the socket to shank strut 11.

This novel adapter arrangement includes adapter fitting 29 which is affixed removably and at least indirectly to socket 28 via a standard extension affixed to the socket. This extension is comprised of a wooden or molded plastic filler block 30. Filler block 30 is formed to receive and be affixed to formed socket 28 and also formed to have within its matrix attachment receiving means such as a commercially available tapped metal plate 31 or, alternatively, an arrangement of threaded inserts. This is accomplished by shaping the lower portion of filler block 30 to match tapped metal plate 31. Then, filler block 30 is laminated over with additional composite 32. Adapter fitting 29 which is permanently attached to mounting plate 33, is, in turn, removably secured to the socket extension by attachment means 34 which is received by receiving means, i.e., tapped metal plate 31.

As shown in FIG. 4, adapter 29 has a tubular cross-section. The lower portion of adapter 29 is received by U-shaped shank strut 11 and secured thereto by attachment means 35. Within adapter 29, horizontally spanning the space between opposite surfaces of the element, there is provided at least one spacer 36, preferably two (one above the other), for receiving attachment means 35.

An alternate approach is to install the tubular element of adapter 29 without mounting plate 33 directly into a tubular clamp type attachment (not shown) which is commercially available. Some commercially available knee mechanisms also have clamping tubular receptacles into which the adapter's, 30 mm diameter tube will directly slide. Also, some commercial tubular clamp mechanisms contain adjustable alignment capability and are of lightweight materials which allow permanent installation to the socket. Thus, it would not be necessary to remove or "transfer out" the alignment componentry after limb alignment.

Figure 5:
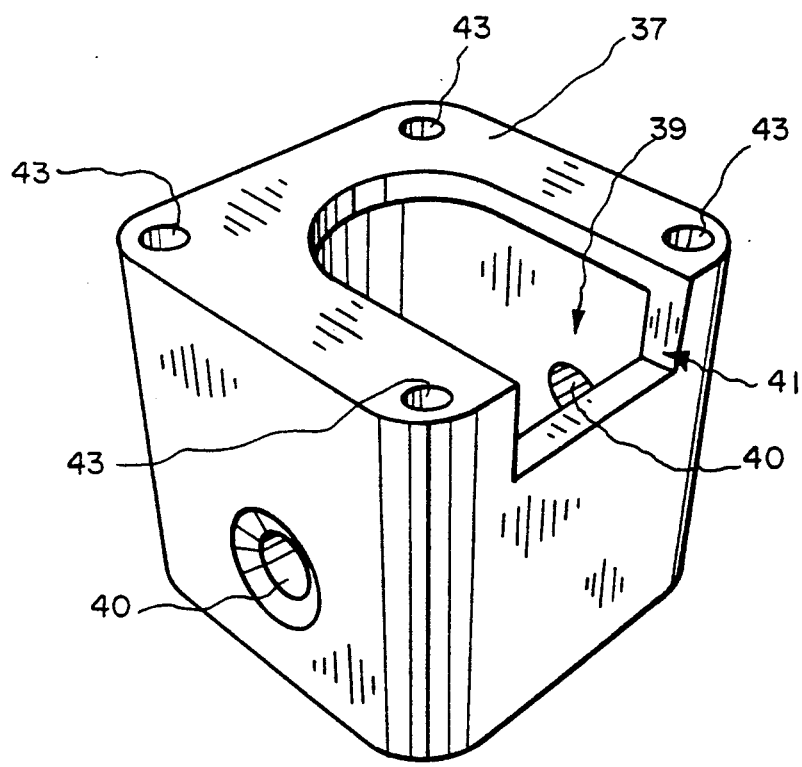
Figure 6:
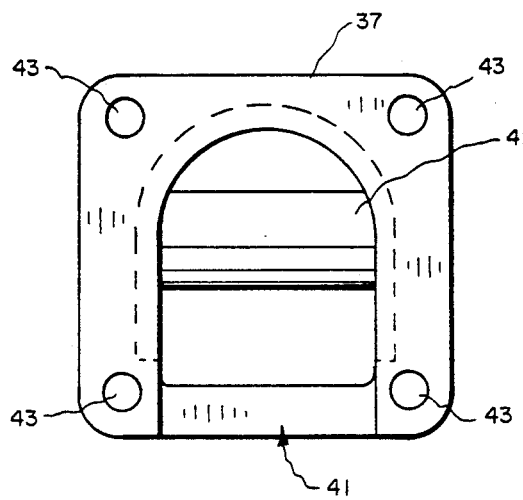
Figure 7:
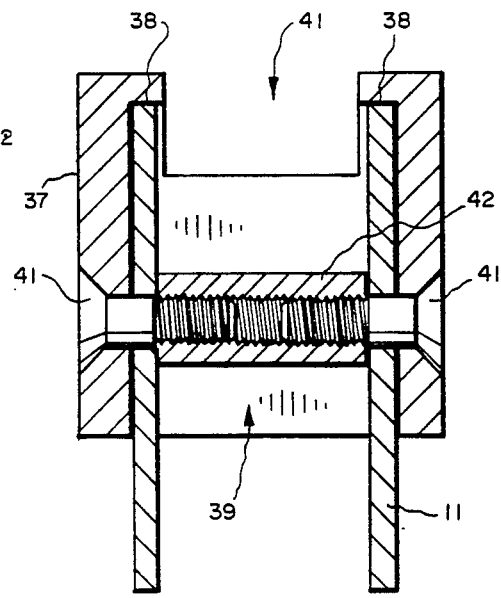
Figure 8:
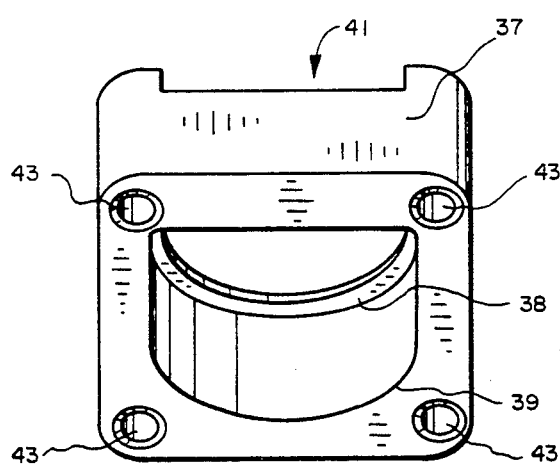

An alternative to adapter fitting 29 is depicted in FIGS. 5, 6, 7, and 8. Made of aluminum or injection molded thermoplastic, e.g., 30% glass filled nylon 6/10, adapter fitting coupling (hereinafter coupling 37) is adapted to receive the upper portion of shank strut section 11. As shown in FIGS. 7 and 8, molded stop 38 is formed from at least a portion of the inside upper margin of receiving recess 39, shown best in FIGS. 7 and 8, in coupling 37. As shown in FIG. 5, coupling 37 has at least one hole 40, preferably two, (one on each side) for receiving at least one but preferably two attachment means. As shown in FIG. 7, attachment means 41 secures shank strut section 11 to coupling 37 to prevent shank strut 11 from dropping out of the fitting. Shown in FIGS. 6 and 7, spacer 42 is preferably provided to maintain the stability of the sides of shank strut 11 and to provide a receptacle for attachment means 41. At least three but preferably four attachment means (not shown) extend through passages 43, shown in FIGS. 5, 6 and 8, and secure coupling 37 to either a commercial alignment tool or a stump socket. If attached to a commercial alignment tool, the angular and linear alignment of prosthesis 10 is adjusted and the alignment tool is then usually transferred out. Alternatively, as shown in FIGS. 5-8, the front wall of coupling 37 preferably has recess 41 for receiving an alignment tool.

The invention also includes the method of producing a foot prosthesis by first forming main member 10 and a separate sole member 15. The preferred construction materials, i.e., composite fiberglass materials, are formed into the U-shaped main section which becomes flattened in the ankle transition zone and curves forwardly into the anterior upper toe section and finally the anterior toe tip. This is done by the usual method of wetting several thick, precut layers of unidirectional and woven cross-plied fiberglass fabrics with resin The wet layers are then positioned in tapered sequence, i.e., laminations, to form said U-shaped shank strut section, said ankle transition zone, and said anterior toe section including anterior upper toe section 13 and anterior toe tip 14. Separate sole member 15 is similarly fashioned. Curing may take place in a vacuum bag and/or at elevated temperatures to expedite the curing process.

Alternatively, the design is suitable for "Resin Transfer Molding" [RTM]techniques where the fibers are precut, placed dry into a mold which is then closed. Then, catalyzed resin is injected into the cavity wherein curing takes place. Still further alternatively, the design is also suitable for injection or compression molding techniques.

Prior art devices have included a wedge of resilient material between a sole member and adjacent main member. The prior art method of constructing this device consisted of first casting a wedge of resilient material, then taking the cured pre-cast wedge and attaching it between the two adjacent members of a prosthesis by securing means such as adhesive. In the preferred method of the invention, the cured fiberglass composite material, i.e., main member 10 and separate sole member 15, are laid generally adjacent and the area between the two is filled with a resilient material that is compatible with fiberglass. The position of the two members may be fixed relative to one another by means of a bonding jig, i.e., a mold. Such resilient material may be liquid polyurethane resin. The liquid resin is first cast into the interface between the anterior toe section of the main member and the plantar toe section of the sole member and then heat cured. Alternatively, the resilient material may be of caulk-like consistency, having added to it material such as fumed silica and/or milled fiberglass filaments to increase its viscosity so that it may be retained where desired without flowing away until it is cure set such as by the application of heat. Regardless of the precise means employed, the novel aspect of the method comprises placing uncured resilient material between the two members of the prosthesis and then curing the resilient material so as to bond the two members of the prosthesis together, thus, eliminating the steps of pre-casting a wedge of resilient material and then securing the wedge in place.

The rear edge location of the elastomer determines the cantilevered heel length of heel section 17. The rear edge location of the elastomer can be controlled. Thus, the cantilevered heel length and heel stiffness can be controlled.

Once the uncured resilient material is in place, the resilient material is cured, forming a good bond between the two pieces of preferred composite material and the resilient material. As with curing main member 10 and sole member 15, curing may take place in a vacuum bag and/or, at elevated temperatures to expedite the curing process.

The prosthesis foot of the present invention has been fabricated as shown in FIG. 1. The device was fitted to a somewhat inactive, above-the-knee amputee and subjected to use representative of a geriatric, i.e., ascending and descending stairs, sitting, and walking indoors and outdoors on somewhat uneven terrain. The instant invention was described by the wearer as having a smooth transition starting with initial heel contact through foot flat and roll over to toe off. The torsional flexibility of the device was described as being exceptionally good, especially when considering that most other commercial prosthesis systems exhibit very little torsional capability whatsoever.

Whereas this invention is here illustrated and described with reference to embodiments thereof presently contemplated as the best mode of carrying out such invention in actual practice, it is to be understood that various changes may be made in adapting the invention to different embodiments without departing from the broader inventive concepts disclosed herein and comprehended by the claims that follow.

I claim:

1. A foot and leg prosthesis comprising,
   (a) an elongate composite main member having a shank strut section, an ankle transition zone, and an anterior toe section including anterior upper toe section and anterior toe tip; said main member being of U-shaped cross-section at its shank strut section; one end of said shank strut section being connected to a socket adapted to receive a residual, amputated leg, the other end smoothly curving forwardly of the shank strut section to said anterior toe tip;
   (b) a sole member having a plantar toe section and a heel section, said plantar toe section including a plantar upper toe section and plantar toe tip, and said heel section including a heel tip, said toe section extending rearwardly from said plantar toe tip substantially along and generally adjacent to said anterior toe section to a point of divergence from where the sole member continues rearwardly to said heel section and heel tip while the anterior upper toe section becomes said ankle transition zone and curves upwardly to the shank strut section; and (c) resilient material cast between the anterior toe section and the plantar toe section substantially through the area where the two segments are generally adjacent, to restrain and control relative movement between the two members.

2. A foot prosthesis according to claim 1, wherein said members are constructed of fiberglass composite materials.

3. A foot prosthesis according to claim 2, wherein the fiberglass composite materials include unidirectional and cross-plied fabrics embedded in a resin matrix selected from the group of resins consisting of orthothalic polyester resin, isothalic polyester resin, epoxy type resins, and mixtures thereof.

4. A foot prosthesis according to claim 2, wherein said main and sole members are constructed of laminations of unidirectional fiberglass composite material extending lengthwise and encapsulated by cross-plied composite material comprised of standard woven fabric layers.

5. A foot prosthesis according to claim 2, wherein at least one face of the vertical shank strut of said main member is treated to protect against splinters by a material selected from the group consisting of gelcoat, fabric, and film.

6. A foot prosthesis according to claim 2, wherein said resilient material is formed from a polyurethane resin.

7. A foot prosthesis according to claim 6 wherein said polyurethane resin is cast as a liquid into the interface between said anterior toe section and said plantar toe section.

8. A foot prosthesis according to claim 1 including an adapter fitting coupling, said coupling having a receiving recess adapted to receive the upper portion of said shank strut.

9. A foot prosthesis according to claim 8 wherein is included a spacer for receiving at least one attachment means for securing said adapter fitting to said shank strut, said spacer spanning the space between opposite inside surfaces of the U-shaped shank strut and providing a supporting member within the shank strut.

10. A foot and leg prosthesis comprising,
(a) an elongate composite main member of fiberglass composite construction having a shank strut section, an ankle transition zone, and an anterior toe section including anterior upper toe section and anterior toe tip; said main member having a U-shaped cross-section at its shank strut section; one end of said shank strut section being connected to a socket adapted to receive a residual, amputated leg, the other end smoothly curving forwardly of the shank strut section to said anterior toe tip;
(b) a sole member of fiberglass composite construction having a plantar toe section and a heel section, said plantar toe section including a plantar upper toe section and plantar toe tip, and said heel section including a heel tip, said toe section extending rearwardly from said plantar toe tip substantially along and generally adjacent to said anterior toe section to a point of divergence from where the sole member continues rearwardly to said heel section and heel tip while the anterior upper toe section becomes said ankle transition zone and curves upwardly to the shank strut section; and
(c) resilient material cast between the anterior toe section and the plantar toe section substantially through the area where the two segments are generally adjacent, to restrain and control relative movement between the two members, said resilient material being formed from a polyurethane resin having added to it material to harden and increase its tear strength, said material being selected from the group consisting of milled glass fiber, fumed silica, and mixtures thereof.

11. A foot and leg prosthesis comprising,
(a) an elongate composite main member having a shank strut section, an ankle transition zone, and an anterior toe section including anterior upper toe section and anterior toe tip; said main member having a U-shaped cross-section at its shank strut section; one end of said shank strut section being connected to a socket adapted to receive a residual, amputated leg, the other end smoothly curving forwardly of the shank strut section to said anterior toe tip;
(b) a sole member having a plantar toe section and a heel section, said plantar toe section including a plantar upper toe section and plantar toe tip, and said heel section including a heel tip, said toe section extending rearwardly from said plantar toe tip substantially along and generally adjacent to said anterior toe section to a point of divergence from where the sole member continues rearwardly to said heel section and heel tip while the anterior upper toe section becomes said ankle transition zone and curves upwardly to the shank strut section;
(c) resilient material cast between the anterior toe section and the plantar toe section substantially through the area where the two segments are generally adjacent, to restrain and control relative movement between the two members; and
(d) an adapter fitting attaching said shank strut section to said socket, said fitting having a tubular cross section and being received by the shank and secured thereto by at least one attachment means.

12. A foot prosthesis according to claim 11 wherein the fitting has within it at least one spacer spanning the space between opposite sides of the fitting, said spacer being adapted to receive attachment means for securing said fitting to said shank strut.

13. A foot prosthesis according to claim 12 including a mounting plate the under surface of which is permanently secured to said adapter fitting and the upper surface of which is secured at least indirectly to a socket.

* * * * *